United States Patent [19]

Czop et al.

[11] Patent Number: 5,057,503
[45] Date of Patent: Oct. 15, 1991

[54] DERIVATIVIZED POLYSACCHARIDES WITH BIOLOGIC ACTIVITY, METHOD OF THEIR ISOLATION, AND USES THEREFOR

[75] Inventors: Joyce K. Czop, Norton; Michael J. Janusz, West Newton, both of Mass.

[73] Assignee: The Brigham and Women's Hospital, Boston, Mass.

[21] Appl. No.: 299,693

[22] Filed: Jan. 23, 1989

[51] Int. Cl.$^5$ .................... A61K 31/00; A61K 39/00
[52] U.S. Cl. .................... 514/54; 514/885; 424/88; 424/89; 424/92; 424/85.8; 424/86; 424/87
[58] Field of Search .................... 514/54, 25, 885; 424/88, 89, 92, 85.8, 86, 87

[56] References Cited

FOREIGN PATENT DOCUMENTS 60-155202 8/1985 Japan .

OTHER PUBLICATIONS

Di Luzio et al., *Int. J. Cancer* 24: 773-779 (1979).
Sherwood et al., *Int. Immunipharmacol.* 9: 261-267 (1987).
Chihara et al., *Cancer Detection Prevent. Suppl.* 1:423-443 (1987).
Sharp et al., *J. Biol. Chem.* 259:11312-11320 (1984).
Sharp et al., *J. Biol. Chem.* 259:11321-11336 (1984).
Janusz et al., *J. Immunol.* 137:3270-3276 (1986).
Her et al., *J. Carbohydr. Chem.* 6:129-139 (1987).
Janusz et al., 4th International Conference of Immunopharmacology, Osaka, Japan, May 18, 1988.

*Primary Examiner*—Ronald W. Griffin
*Assistant Examiner*—Everett White
*Attorney, Agent, or Firm*—Sterne, Kessler, Goldstein & Fox

[57] ABSTRACT

This invention relates to the discovery and isolation of the smallest biologically active polysaccharide which will interact with the β-glucan receptors present on mammalian phagocytic cells. The invention additionally relates to methods of preparing this heptaglucoside, and uses of the molecule as an immunomodulator and an activating agent. The invention additionally relates to methods of separating biologically active polysaccharides from similar inactive forms, and improved methods of separating low molecular weight polysaccharides and isomers from one another.

17 Claims, 8 Drawing Sheets

DERIVATIZED POLYSACCHARIDES WITH BIOLOGIC ACTIVITY, METHOD OF THEIR ISOLATION, AND USES THEREFOR

BACKGROUND OF THE INVENTION

This invention was made using funds of the United States Government under National Institutes of Health grants AI 23542 and AI 22834. The U.S. Government has certain rights in this invention.

FIELD OF THE INVENTION

This invention is in the field of carbohydrate chemistry and immunology. It relates to the preparation of isolated complex polysaccharides which are active in mammalian biologic systems. Specifically, the invention relates to the preparation, isolation, and biologic use of a derivatized yeast heptaglucoside that is the smallest sized functional unit to interact with the β-glucan receptors present on mammalian phagocytic cells.

DESCRIPTION OF THE RELATED ART

Polysaccharides are carbohydrate polymers in which the repeating units or building blocks are sugars. The manner in which the glucose units are joined controls their biologic activity.

As is readily apparent to those skilled in the art of carbohydrate chemistry, separation of low molecular weight polysaccharides that differ in size by one or two glucose units is a difficult task for two reasons: first, the chemical subunits are identical, and second, the manner in which, for example, seven glucose units can be joined yields well over a hundred different heptaglucosides. Thus, process designs that separate biologically active heptaglucosides from chemically similar inactive forms are highly desirable for obtaining large amounts of isolated materials for the development of drugs, for example.

β-glucans are the major structural components of yeast and fungal cell walls (Bartnicki-Garcia, S., *Ann. Rev. Microbiol.* 22:87 (1968)). Manners et al. (*J. Gen. Microbiol.* 80:411 (1974)) have demonstrated that the cell wall glucans of *S. cerevisiae* consist of two basic types of β-glucans: major components comprised of consecutively 1,3-linked glucose residues with small numbers of 1,6-linked branches, and minor components with consecutive 1,6-linkages and 1,3 branches.

Glucans are also active pharmacologic agents in host defense systems of plants (Albersheim, P. et al., *J. Cell. Biol.* 78:627 (1978)) and animals (Di Luzio, N.R., *Trends Pharmacol. Sci.* 4:344 (1983)). Soluble β-glucans isolated from *Phytophthora megasperma* (Ayers, A.R. et al., *Plant Physiol.* 57:760 (1976)) and *Saccharomyces cerevisiae* (Hahn, M.G. et al., *Plant Physiol.* 62:107 (1978)) stimulate plants to synthesize antibiotics, termed phytoalexins, which are static or toxic to a broad spectrum of microorganisms (Albersheim, P. et al., *J. Cell. Biol.* 78:627 (1978)).

β-glucans are also polyglucose immunomodulators. The administration of particulate glucans purified from S. cerevisiae to laboratory animals induces host resistance to a variety of lethal pathogens (Reynolds, J.A. et al., *Infect. Immun.* 30:51 (1980)) by mechanisms involving macrophage stimulation (Di Luzio, N.R. et al., *J. Reticuloendothel. Soc.* 7:731 (1970)). The β-glucan constituents of *S. cerevisiae* cell walls are recognized by human monocytes, as evidenced directly by monocyte phagocytosis of purified glucan particles (Czop, J.K. et al., *Proc. Natl. Acad. Sci. USA* 82:2751 (1985)) and indirectly by the functional impairment of monocyte responses to particulate glucan and zymosan by soluble β-glucans isolated from yeast extract and sonicated glucan particles (Janusz, M.J. et al., *J. Immunol.* 38:3897 (1987); Janusz, M.J. et al., *J. Immunol.* 137:3270 (1986)). In vitro studies reveal that bone marrow-derived mouse macrophages (Kadish, J.L. et al., *Immunol. Res.* 5:129 (1986)) and human peripheral blood monocytes (Czop, J.K. et al., *Proc. Natl. Acad. Sci. USA* 82:2751 (1985); Janusz, M.J. et al., *J. Immunol.* 138:3897 (1987)) possess β-glucan receptors that mediate phagocytosis of glucan particles and induce release of proinflammatory mediators in the absence of opsonic plasma proteins. Glucose is the sugar unit contained in polysaccharides that interact with β-glucan receptor on mammalian phagocytic cells.

Of the fungal β-glucans, lentinan, a high molecular weight derivative of mushrooms, is similar in chemistry to yeast β-glucans and has been shown to have immunomodulating activity (Chihara et al., *Cancer Detection Preven. Suppl.* 1:423 (1987)).

Zymosan particles are cell wall derivatives of *S. cerevisiae* which are similar in size and carbohydrate composition to glucan particles except that they contain small amounts of α-mannans (Di Carlo, F.J. et al., *Science* 127:756 (1958); Bacon, J.S.D. et al., *Biochem. J.* 114:557 (1969)). The ingestion of zymosan particles by murine macrophages (Kadish, J.L. et al., *Immunol. Res.* 5:129 (1986)) is inhibited by soluble β-glucans with 1,3 and 1,6 linkages but not by soluble yeast α-mannans that have been rendered free of contaminating yeast β-glucans.

Human monocyte phagocytosis of zymosan particles is also selectively inhibited by a variety of non-yeast-derived β-D-glucans which are chemically and structurally similar to those present in cell walls of *S. cerevisiae*. Phagocytosis is not inhibited by homopolysaccharides containing epimers of glucose, such as mannose and galactose, or homoglucosyl polysaccharides with α-anomeric linkages or β,1,4 linkages (Czop, J.K. et al., *J. Immunol.* 134:2588 (1985); Czop, J.K. et al., *J. Immunol.* 135:3388 (1985)). That only some low molecular weight yeast oligoglucosides (Janusz, M.J. et al., *J. Immunol.* 137:3270 (1986)) functionally impair monocyte phagocytic responses to zymosan particles adds a further level of specificity to monocyte β-glucan receptors.

The β-glucan constituents of zymosan stimulate monocyte synthesis of leukotrienes $B_4$ and $C_4$ (Czop, J.K. et al., *Proc. Natl. Acad. Sci. USA* 82:2751 (1985)) and secretion of the lysosomal enzyme β-N-acetyl-glucos-aminidase (Janusz, M.J. et al., *J. Immunol.* 138:3897 (1987)). Monocyte β-glucan receptors are exquisitely sensitive to inactivation by trypsin (Czop, J.K. et al., *J. Immunol.* 120:1132 (1978)) and are functionally distinct from Fc receptors for IgG, complement type 1 receptors, fibronectin receptors (Czop, J.K. et al., *J. Immunol.* 134:2588 (1985)), and complement type 3 receptors (Czop, J.K., *Pathol. Immunopathol. Res.* 5:286 (1986)).

Partial acid hydrolysates of soluble yeast glucan-derived β-glucans contain oligoglucosides with an $M_r < 4,000$, some of which inhibit monocyte ingestion of zymosan particles (Janusz, M.J. et al., *J. Immunol.* 137:3270 (1986)).

INFORMATION DISCLOSURE STATEMENT

Di Luzio et al., Int. J. Cancer 24:773–779 (1979) and Sherwood et al., Int. Immunopharmacol. 9:261 (1987) describe the biologic influence of soluble and particulate glucan on tumor and bacterial activity and cytokine activation, respectively. In both papers, mixtures of soluble glucans are prepared by boiling yeast glucan in 90% formic acid. No steps were taken to separate soluble forms.

Chihara et al., Cancer Detection Prevent. Suppl. 1:423–443 (1987) describes antitumor and metastasis-inhibitory activities of lentinan. The investigators prepared a sparingly soluble mixture of high molecular weight $\beta$-glucans from mushrooms.

Sharp et al., J. Biol. Chem. 259:11312–11320 (1984) and Sharp et al., J. Biol. Chem. 259:11321–11336 prepared acid soluble glucans from fungal cell walls and separated glucose polymers by Bio-Gel P-4, Bio-Gel P-2, and HPLC. Their isolation procedure used a method of measurement called refractive index, which requires very large amounts of polysaccharides. Sharp et al. were interested in the smallest sized polysaccharides that stimulate plants to synthesize antibioticlike substances called phytoalexins, isolated a small polymer active in the plant system, and characterized it as a fungal $\beta$-D-heptaglucoside. Sharp's method did not include derivatization with 2-aminopyridine.

Sharp's fungal heptaglucoside elutes in a different fraction than the derivatized yeast heptaglucoside described by the present invention and, with or without derivatization, the fungal heptaglucoside does not interact with human monocyte $\beta$-glucan receptors.

Janusz et al., J. Immunol. 137:3270–3276 (1986), prepared various types and sizes of soluble yeast glucans, including those solubilized by acid and separated by Bio-Gel P-4 columns; no purification steps beyond Bio-Gel P-4 and no derivatization with 2-aminopyridine are described.

Her et al., J. Carbohydr. Chem. 6:129–139 (1987), describe a derivatization procedure with 2-aminopyridine and commercially available polysaccharides of known chain length and structure. Her's interest is in improving the derivatization procedure, and not in deducing biologic activity. There is no assessment of biologic activity or toxicity of derivatized polymers in this paper.

Janusz et al., 4th International Conference of Immunopharmacology, Osaka, Japan, May 18, 1988. The inventors presented a 10-minute talk on the isolation of the derivatized yeast heptaglucoside. Derivatization of acid-solubilized yeast glucans with 2-aminopyridine immediately before the HPLC step was disclosed.

Japanese Patent Abstract Application No. 60155202, filed Aug. 15, 1985, and assigned to Toyo Soda Mfg., describes an antitumoral chemically modified polysaccharide. The chemical procedure utilized in the Japanese application is significantly different from the method of the present invention. The reaction in the Japanese application involves formation of a Shiff's base rather than a dehydration reaction. In addition, 4-aminopyridine is used in the Japanese application, instead of 2-aminopyridine as in the present invention. There is no indication in the Japanese application that basic antitumor activity was actually influenced by the chemical procedure.

SUMMARY OF THE INVENTION

The inventors originally undertook the studies described by the present invention in order to isolate the functionally smallest or unit ligand in S. cerevisiae cell walls recognized by mammlian phagocytic cell $\beta$-glucan receptors. During these studies, they discovered this smallest biologically active polysaccharide, as well as methods useful in stimulating $\beta$-glucan receptors, and various uses for this heptaglucoside, as described below.

In conducting these experiments, the inventors also discovered an improved method for separating low molecular weight (LMW) polysaccharides from one another. As is readily apparent to those skilled in the art of carbohydrate chemistry, the separation of LMW polysaccharides that differ in size by only a few glucose units is a difficult task for two reasons: first, the chemical subunits are identical, and second, the manner in which, for example, seven glucose units can be joined, yields well over a hundred different heptaglucosides. The inventors have discovered a process which separates biologically active heptaglucosides from chemically similar inactive forms which will be highly useful for obtaining large amounts of certain isolated materials useful for drug development, for example.

Specifically, the invention has general applicability in that it provides a very sensitive method for generating and isolating any polysaccharide of interest that has a reducing end sugar.

A reducing end sugar is the one for which the hydroxyl of the anomeric carbon (with yeast polymers of glucose, that is almost always the first carbon) is free. It is unsubstituted; it is not linked to another glucose. In the present invention, it interacts with 2-aminopyridine and provides a means of detection (Her et al., J. Carbohydr. Chem. 6:129 (1987)).

More importantly, this chemical interaction increases the potency of a molecule which already has biologic activity, which was completely unexpected. The reason this happens is because derivatization stabilizes the reducing sugar, which normally can be an open- or closed-ring structure, to a closed-ring structure to which the 2-aminopyridine is covalently linked (Her et al., J. Carbohydr. Chem. 6:129 (1987)). This chemical procedure improves potency and *does not confer toxicity* to mammalian cells.

If, for example, one were interested in a polysaccharide that affected liver cells, the derivatized form of that polysaccharide would mediate that effect better. Alternatively, in the above example with liver cells, if the derivatized polysaccharide of interest reversed the response of interest without killing the liver cells, as assessed by an independent method, the data would be useful in identifying the free reducing-end sugar as a component necessary for the response under investigation (the free reducing end would not be available because of its derivatization with 2-aminopyridine).

In short, this invention has general applicability in that it provides a very sensitive method for generating and isolating any polysaccharide of interest that has a reducing end sugar. The invention has general applicability to polysaccharides of biomedical interest not only in their further purification but also in identifying the portion of the polysaccharide molecule which confers activity, thus filling a distinct void in the art.

The inventors have isolated the smallest biologically active polysaccharide which will interact with $\beta$-glucan receptors on mammalian phagocytic cells. The inventors have found that derivatization of this heptaglucoside with 2-aminopyridine increases the capacity of the molecule to stimulate β-glucan receptors by approximately 70-fold (in addition to potentiating functions mediated by these receptors), but does not confer activity to inactive polysaccharides. In fact, the inventors have discovered that in terms of weight, the active heptaglucoside is 40,000 times more active than an unfractionated mixture of solubilized polysaccharides in interacting with β-glucan receptors, and 1,000 times more active than any other compound thus far described with such a function.

Accordingly, the present invention provides a novel heptaglucoside, the method for the derivatization thereof, and methods for the use of the heptaglucoside, for example as an immune adjuvant. The invention further includes immune response-provoking compositions comprising the heptaglucoside. This invention is useful for vaccine or other immunomodulating agent preparations, which may then be used, for example, in adjuvant therapy and the like.

For example, the heptaglucoside described by the present invention may be used as an adjuvant to increase nonspecific host resistance to bacteria, viruses, protozoans, helminths, fungi, and other various organisms parasitic in the host for whom the adjuvant therapy is intended, as well as aiding in the reduction or elimination of tumors, for example in the treatment of cancer, and in boosting the immune response of cancer patients post surgery, chemo- or radiotherapy.

The heptaglucoside of the present invention may also be used as an adjuvant to increase the host's specific immune response. In fact, any immune response mediated by activated phagocytic cells may be potentiated using the derivatized heptaglucoside of the present invention.

The heptaglucoside of the present invention is also useful as an immune adjuvant to enhance immune responses in individuals at a much lower concentration than the previously available preparations.

It should be understood that the derivatization of the heptaglucoside, as taught by the present invention, generally can increase the potency of any pharmacologically active polysaccharide, discussed more fully below.

The manner in which these and other objects are realized by the present invention will be apparent from this summary and the detailed description set forth below.

To isolate the heptaglucoside, or unit ligand recognized by phagocytic cell β-glucan receptors, acid-solubilized oligoglucosides were prepared by the partial acid hydrolysis of purified yeast cell walls, gel filtered sequentially on Bio-Gel P-4 and twice on P-2, derivatized with 2-aminopyridine, and separated by normal-phase highperformance liquid chromatography (HPLC). Ligand recognition was assessed by quantitating the effect of pretreatment with isolated materials to the capacities of adherent monocytes to phagocytose zymosan particles (the phagocytosis-inhibiting activity), and analyzed by fast-atom-bombardment (FAB) mass spectrometry.

The unit ligand isolated is a heptaglucoside which is functionally unrelated to a structurally defined β-heptaglucoside that stimulates plant phytoalexin synthesis (Sharp, J.K. et al., *J. Biol. Chem.* 259:11341 (1984)). Partial acid hydrolysis solubilized 23±4% (mean±SD, n=7) of the cell wall glucans; at an input of 50 μg/ml, the solubilized products reduced monocyte ingestion of zymosan particles by an average of 44%.

Gel filtration of acid-solubilized glucans on Bio-Gel P-4 revealed several peaks with phagocytosis-inhibiting activity, and fractions from the peak containing the smallest oligoglucosides, which accounted for 10±2% (mean±SD, n=7) of the carbohydrate applied, were pooled. Further purification on Bio-Gel P-2, twice, resolved this phagocytosis-inhibiting activity to a single peak which contained apparent heptoses and accounted for 8±2% (mean±SD, n=6) of the a carbohydrate applied. At a concentration of 0.5 μg/ml, the oligoglucosides pooled from the Bio-Gel P-4 and P-2 columns reduced monocyte ingestion to plateau levels of 45±1% and 42±7% (mean±SD, n=3), respectively.

When derivatized with 2-aminopyridine, the oligoglucosides were resolved by HPLC to a number of peaks; a peak that eluted as an apparent heptaglucoside contained virtually all the inhibitory activity and accounted for only 6.6±0.7% (mean±SD, n=7) of the carbohydrate applied to the column. Gas chromatography (GC) analysis revealed only glucose, and FAB-mass spectrometric analysis showed only heptaglucoside and no non-carbohydrate molecules. At a concentration of 1.6 ng/ml, the derivatized yeast heptaglucoside reduced monocyte ingestion of zymosan to plateau inhibitory levels of 44±9% (mean±SD, n=5) (FIG. 7). There is a linear dose-effect from 0.4 to 1.6 ng/ml. By a scale-up procedure which involves two Bio-Gel P-2 columns, described below, the isolated heptaglucoside will at 0.1 ng/ml (100 pg/ml) effect similar plateau inhibitory levels; 50 pg/ml is approximately half as effective. Thus, the heptaglucoside discovered by the inventors to be present in yeast cell walls is a unit ligand for human monocyte β-glucan receptors.

The present invention provides the discovery and isolation of the smallest or unit ligand in yeast cell walls recognized by mammalian phagocytic cell β-glucan receptors.

The present invention also provides a method for increasing the capacity of polysaccharides, in particular yeast heptaglucosides, to interact with the β-glucan receptors present on mammalian phagocytic cells.

The present invention also relates to the potentiation of functions mediated by β-glucan receptors by contacting the derivatized heptaglucoside of the present invention with the receptors via normal fluid-phase interactions of the active material with cell surface protein receptors. The method described by the present invention may be used to increase the potency of any pharmacologically active polysaccharides.

The present invention also provides a therapeutic method for immunomodulation in a subject comprising administering to said subject in need of such immunomodulation the derivatized heptaglucoside of the present invention in an amount sufficient to stimulate phagocytic cell activity.

It also provides a method for the treatment of microbial infection, comprising administering to a subject in need of such treatment a pharmaceutical composition comprising a therapeutically effective amount of the heptaglucoside, and a pharmaceutically acceptable carrier.

The present invention also provides a method of enhancing an immune response to an antigen in a subject comprising administering to said subject in need of an enhanced immune response an amount of the heptaglucoside in an amount sufficient to enhance the immune response of said subject to said antigen.

The invention also provides a method of separating LMW polysaccharides that differ in size by at least one glucose unit, in order to separate biologically active polysaccharides from chemically equivalent inactive forms. This ability will facilitate the isolation of large amounts of desired material, for example. This would be accomplished by solubilizing the source that exhibits activity and subjecting the soluble complex polysaccharide to gel-filtration on, for example, polyacrylamide gel matrices, followed (or preceded) by derivatization and HPLC.

In particular, the invention is directed to a heptaglucoside, with a molecular weight of approximately 1,000 daltons, capable of interacting with $\beta$-glucan receptors on mammalian phagocytic cells.

The invention is additionally related to the heptaglucoside described above, obtained from yeast.

The invention also includes the 2-aminopyridine derivative of the heptaglucoside described above.

The invention also includes a method for obtaining the smallest biologically active polysaccharide which will interact with $\beta$-glucan receptors on mammalian phagocytic cells comprising:
(a) solubilizing particulate glucans in yeast cell walls;
(b) recovering the fraction of step (a) that contains biologic activity;
(c) subjecting the product obtained in step (b) to chromatographic fractionation;
(d) derivatizing the fractionated biologically active fraction obtained in step (c) with 2-aminopyridine; and
(e) subjecting the derivatized fraction obtained in step (d) to chromatographic fractionation.

The invention additionally includes the method as above wherein step (e) further comprises subjecting said chromatographically fractionated derivatized product from step (d) to high performance liquid chromatography to obtain the substantially pure heptaglucoside product.

The heptaglucoside of the present invention can also be obtained by derivatizing the solubilized product any time prior to a final chromatographic fractionation step, such as HPLC. In this case, such method would comprise:
(a) solubilizing particulate glucans in yeast cell walls;
(b) derivatizing the solubilized product obtained in step (a) with 2-aminopyridine; and
(c) subjecting the derivatized product obtained in step (b) to chromatographic fractionation.

The chromatographic fractionation step (c) may include a four-step procedure involving subjecting the derivatized product to Bio-Gel P-4, two runs on Bio-Gel P-2, and HPLC.

The invention additionally includes the smallest biologically active polysaccharide which will interact with $\beta$-glucan receptors on mammalian phagocytic cells, obtained by the method described above.

The invention additionally includes the smallest biologically active polysaccharide which will interact with $\beta$-glucan receptors which is a heptaglucoside.

The invention additionally includes the above-described heptaglucoside wherein said heptaglucoside may be used as an immunomodulating agent.

The invention additionally includes the above-described heptaglucoside which is useful as an immune adjuvant.

The invention additionally includes the use of the abovedescribed heptaglucoside in immune adjuvant therapy such as surgery, chemotherapy, and radiotherapy.

The invention additionally relates to a therapeutic method for immunomodulation in a subject comprising administering to said subject in need of such immunomodulation the heptaglucoside described above, in an amount sufficient to stimulate mammalian phagocytic cell activity.

The invention additionally includes a method of increasing the potency of a pharmacologically active polysaccharide by derivatizing said polysaccharide with 2-aminopyridine.

The invention is also related to a method of enchancing an immune response to an antigen in a subject comprising administration of an amount of the heptaglucoside described above to said subject in an amount sufficient to enhance the immune response of said subject to said antigen.

The invention also relates to a pharmaceutical composition useful for inducing the production of antibodies to an antigen in a subject comprising an immunogenically effective amount of an antigen and the heptaglucoside described above wherein said amount of said heptaglucoside is present in an amount sufficient to enhance the immune response of said subject to said antigen.

The invention additionally includes the pharmaceutical composition described above, wherein said subject is a human.

The invention also relates to a method of preparing a vaccine comprising providing an effective amount of an antigenic and immunogenic preparation of an infectious organism and the heptaglucoside described above as an adjuvant, and dissolving or dispersing effective amounts of said components in a physiologically tolerable carrier and/or diluent.

The invention also is directed to a kit for a vaccine comprising ampoules or the like with:
(a) an effective amount of an antigenic and immunogenic preparation of an infectious organism selected from the group consisting of bacteria, viruses, protozoa, helminths, yeast, fungi, and other organisms which are parasitic in a host;
(b) an effective amount of the heptaglucoside described above to act as an adjuvant; and
(c) a physiologically tolerable carrier and/or diluent for dissolving or dispersing said antigenic and immunogenic preparation and said interferon.

The invention additionally includes a method for activating the $\beta$-glucan receptors on mammalian phagocytes cells comprising derivatizing a biologically active glucan heptaglucoside with 2-aminopyridine.

The invention additionally includes a method for activating the $\beta$-glucan receptors on mammalian phagocytic cells comprising:
(a) solubilizing the particulate glucans in yeast cell walls;
(b) recovering the biologically active fraction obtained in step (a);
(c) subjecting the product obtained in step (b) to chromatographic fractionation;
(d) derivatizing the fractionated biologically active glucan product obtained in step (c) with 2-aminopyridine;
(e) subjecting the derivatized fraction obtained in step (d) to chromatographic fractionation; and (f) contacting the biologically active fraction obtained in (e) with β-glucan receptors on mammalian phagocytic cells.

The invention additionally includes mammalian phagocytic cells which are monocytes, macrophages, or neutrophils. The invention additionally includes mammalian phagocytic cells which are human phagocytic cells. The invention additionally includes a method of increasing the potency of a pharmacologically active polysaccharide comprising derivatizing said polysaccharide with 2-aminopyridine.

The inventors have also discovered an improved method for separating LMW polysaccharides, which differ in size by only a few glucose units. Therefore, this invention teaches an improved method for the large-scale purification and isolation of biologically active polysaccharides, for example.

Accordingly, the invention additionally includes a method for obtaining the separation of low molecular weight polysaccharide molecules, differing in composition by one glucose unit, comprising:
(a) derivatizing said molecules with 2-aminopyridine;
(b) subjecting the products obtained in step (a) to chromatographic fractionation; and
(c) recovering the desired fraction obtained from step (b).

The invention is also directed to a method for obtaining the separation of isomers of low molecular weight polysaccharide molecules comprising:
(a) derivatizing said molecules with 2-aminopyridine;
(b) subjecting the products obtained in step (a) to chromatographic fractionation; and
(c) recovering the desired fraction from step (b).

The invention is also directed to a method for separating biologically active polysaccharide molecules from chemically similar inactive polysaccharide molecules comprising:
(a) solubilizing said polysaccharide molecules;
(b) recovering the active fraction obtained in step (a);
(c) subjecting the product obtained in step (b) to chromatographic fractionation to obtain a biologically active fraction;
(d) derivatizing the fractionated biologically active product of step (c) with 2-aminopyridine; and
(e) subjecting the derivatived product obtained in step (d) to chromatographic fractionation
wherein said polysaccharide is obtained from a cell wall.

Unless defined otherwise, various terms used herein have the same meaning as is well understood in the art to which the invention belongs. All cited publications are incorporated herein by reference.

DETAILED DESCRIPTION OF THE INVENTION

Figure 1:
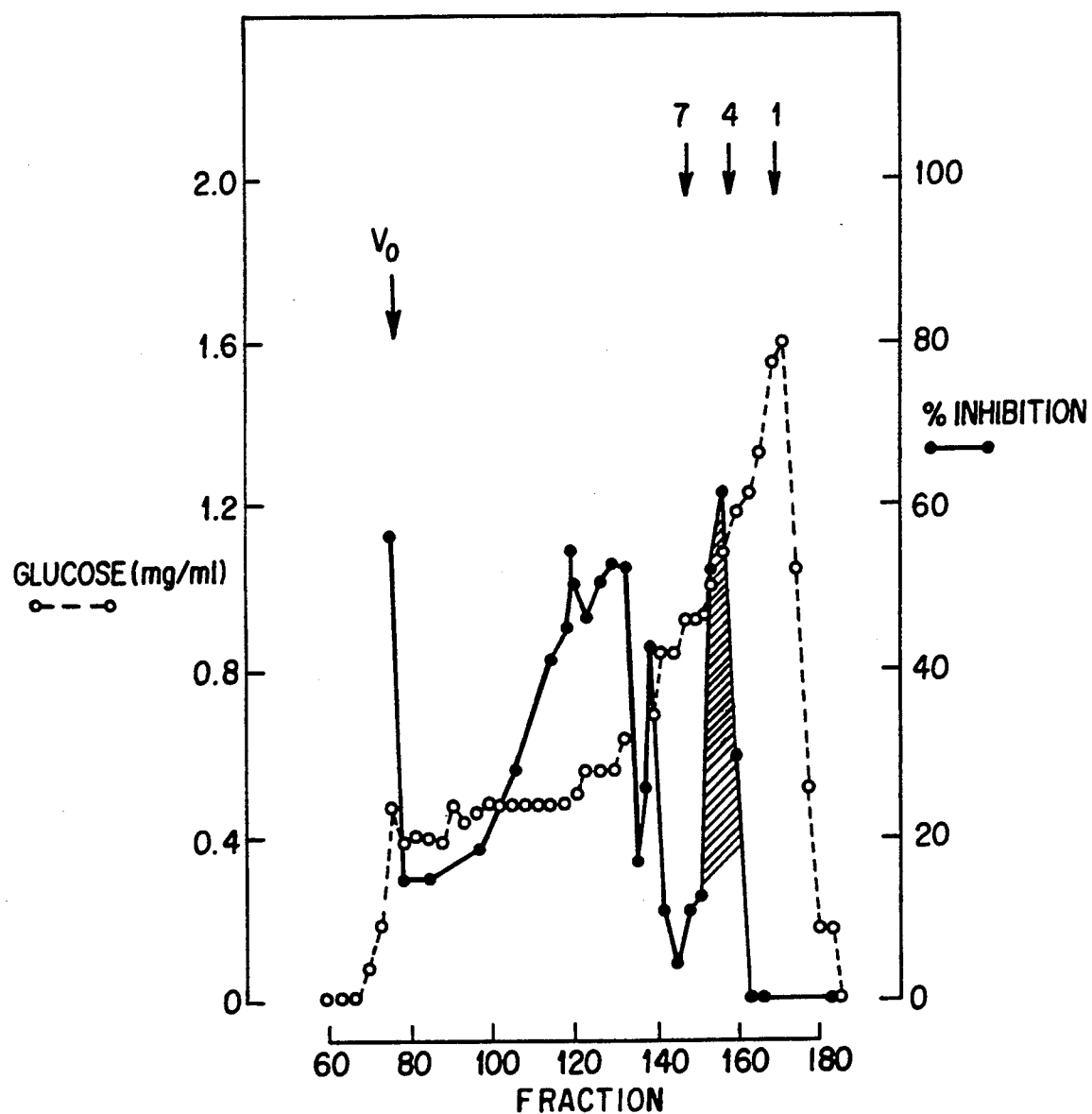
FIG. 1. Filtration of acid-solubilized yeast glucan on Bio-Gel P-4. Fractions were assessed for glucose content (o---o) and for effects on monocyte phagocytosis of zymosan particles (●---●). The positions of the void volume ($V_o$), the eluting peaks of maltoheptose, maltotetrose and glucose standards, and the fractions pooled (shaded area), are indicated. The percentage of monocytes ingesting zymosan after preincubation with buffer alone was 54% and the sample fractions were tested at a concentration of 50 μg/ml of hexose equivalents.

This invention is directed toward the discovery of a heptaglucoside, derived from yeast cell wall particulate glucan, which is the smallest biologically active polysaccharide capable of interacting with the β-glucan receptors on mammalian phagocytic cells, and the substantially pure form of the heptaglucoside. The invention is also directed toward a method of isolating this heptaglucoside, uses of this heptaglucoside as an immunomodulator, methods of separating biologically active polysaccharides from chemically similar inactive forms, and separating LMW polysaccharides from each other.

Specifically, the invention relates to the preparation and isolation of a derivatized yeast heptaglucoside that is the smallest sized functional unit to interact with the β-glucan receptors present on mammalian phagocytic cells. The invention has general applicability in that it provides a very sensitive method for generating and isolating any polysaccharide of interest that has a reducing end sugar.

More importantly, this chemical interaction increases the potency of a molecule which already has biologic activity, which was completely unexpected. The reason this occurs is because derivatization stabilizes the reducing sugar, which normally can be an open- or closed-ring structure, to a closed-ring structure to which the 2-aminopyridine is covalently linked (Her et al., *J. Carbohydr. Chem.* 6:129 (1987)). This chemical procedure improves potency and *does not confer toxicity* to mammalian cells.

In short, this invention has general applicability in that it provides a very sensitive method for generating and isolating any polysaccharide of interest that has a reducing end sugar. The invention has general applicability to polysaccharides of biomedical interest not only in their further purification but also in identifying the portion of the polysaccharide molecule which confers activity, thus filling a distinct void in the art.

By the term "biologically active" or "activate" or "interact with" is meant the capacity of a soluble material to bind to $\beta$-glucan receptors present on any mammalian phagocytic cell, and to initiate responses mediated by those receptors. This term is also meant to include the initiation of defense responses of the activated phagocytic cells to antigens. The heptaglucoside described by the present invention can therefor affect, without limitation, the secretion of lysosomal enzymes, the synthesis of leukotrienes, the production of cytokines such as colony stimulating factor (CSF) for granulocytes/macrophages (GM-CSF), and monocyte/macrophages (M-CSF), and interleukins 1 and 2, for example.

By the term "mammal" is meant any warm-blooded animal which possesses $\beta$-glucan receptors on any of its cells, in particular reticuloendothelial cells. Foremost among such mammals are humans; however, the invention is not intended to be so limiting, it being within the contemplation of the invention to treat any and all mammals which may experience the beneficial effects of the invention.

Experiments performed with soluble yeast glucans of high molecular weight (20-200 kDa) indicate that human neutrophils (Czop et al., *J. Immunol.* 141:3170 (1988)) and mouse macrophages (Goldman et al., *Exp. Cell. Res.* 174:481 (1988)) have $\beta$-glucan receptors. Since the ontogeny of different types of phagocytic cells involve common differentiation pathways until late in the maturation process, the heptaglucoside of the present invention can be recognized and activated generally by mammalian phagocytic cells. Therefore, the term "phagocytic cell" encompasses all mammalian phagocytic cells, including, without limitation, monocytes, macrophages, and neutrophils.

It should be noted that $\beta$-glucans are major constituents of many yeasts and fungi. Of the fungal $\beta$-glucans, lentinan, a high molecular weight derivative of mushrooms, is similar in chemistry to yeast $\beta$-glucans and has been shown to have immunomodulating activity (Chihara et al., *Cancer Detection Preven. Suppl.* 1:423 (1987)). Thus, because "yeast-like" $\beta$-glucans are present in fungi, and have biologic activity, the teaching of the present invention, in all respects, is also applicable to fungi. Therefore, "yeast" and "fungus" may be used interchangeably within this application. For example, fungal $\beta$-glucans which will interact with $\beta$-glucan receptors present on mammalian phagocytic cells include, but are not limited to, fungal $\beta$-glucans.

The heptaglucoside of the present invention is characterized as having immune adjuvant activity, containing about 100% carbohydrate per dry weight, and only glucose residues. It has been characterized by NMR as one isomer.

For purposes of the present invention, one method for obtaining the biologically active heptaglucoside of the present invention which is illustrative, without being limiting, consists of the following steps:

A first step would include extraction and solubilization of the heptaglucoside fraction from a biological sample. The disruption and solubilization of the described heptaglucoside by physical means may be accomplished by prolonged sonication. Disruption by chemical means may be accomplished by enzyme hydrolysis, for example, using $\beta$-glycosidases, or preferably, limited acid hydrolysis, using trifluoroacetic acid. Modifications and alternatives to the above will be clear to one of ordinary skill in the art, without undue experimentation.

A second step would include subjecting the solubilized material to gel chromatography, a type of partition chromatography in which separation of molecules is based on molecular size. Dextran, polyacrylamide, and agarose gels are commonly used for this type of separation. Chromatographs useful in the present invention include Bio-Gel P-4 and P-2. One embodiment would include a 3-tiered chromatographic fractionation including Bio-Gel P-4, Bio-Gel P-2, and a second Bio-Gel P-2 fractionation. However, other methods may be used which effectively separate molecules based on their sizes.

A third step would include subjecting the chromatographed and active fractions to derivatization with 2-aminopyridine. A method for such derivatization is disclosed in Her et al., *J. Carbohydr. Chem.* 6:129 (1987). This derivatization step may actually be performed prior to chromatographic fractionation. Derivatization before or after fractionation maximizes biologic activity of the isolated active materials. However, it may be more convenient to derivatize following fractionation.

A fourth step would include subjecting the product obtained by the above derivatization process to a further chromatographic step, such as normal-phase HPLC.

The heptaglucoside described by the present invention is additionally meant to include variants, analogues, or chemical derivatives thereof which are capable of interacting with mammalian phagocytic cell $\beta$-glucan receptors, and which should be considered equivalent.

The term "variant" of a molecule such as the heptaglucoside of the present invention is meant to refer to a naturally occurring molecule substantially similar to either the entire molecule, or a fragment thereof. An "analogue" of a molecule such as the heptaglucoside of the present invention is meant to refer to a nonnatural molecule substantially similar to either the entire molecule or a fragment thereof.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharma-* ceutical Sciences (1980) and will be apparent to those of ordinary skill in the art.

One screening method for determining whether a given compound is a functional derivative of the heptaglucoside of the present invention comprises, for example, immunoassays employing RIA or ELISA methodologies, based on the production of specific neutralizing antibodies (monoclonal or polyclonal) to the natural heptaglucoside of the present invention. Other suitable screening methods will be readily apparent to those of skill in the art.

The invention is also directed to compositions, such as immunologic compositions, comprising one or more heptaglucoside fractions, and methods of using these compositions as immune adjuvants. For example, the heptaglucoside of the present invention will be useful in immune adjuvant therapy following cancer surgery, chemotherapy, radiotherapy and the like.

By the term "immunomodulator" is meant an agent or molecule capable of modifying an immune response in a subject.

The term "immune adjuvant," as used herein, refers to compounds which, when administered to a subject or tested in vitro, increase the immune response to an antigen in the subject or test system to which said antigen is administered. Some antigens are weakly immunogenic when administered alone or are toxic to the subject at concentrations which evoke immune responses. An immune may enhance the immune response of the subject to the antigen ng the antigen more strongly immunogenic. The adjuvant effect may also lower the dose of said antigen necessary to achieve an immune response in said subject.

For example, the invention includes a method for activating the β-glucan receptors on mammalian phagocytic cells comprising:

(a) solubilizing the particulate glucans in yeast cell walls;
(b) subjecting the solubilized glucan product obtained in step (a) to chromatographic fractionation;
(c) derivatizing the fractionated glucan product obtained in step (b) with 2-aminopyridine;
(d) subjecting the derivatized product obtained in step (c) to chromatographic fractionation; and
(e) contacting the derivatized product of step (d) with β-glucan receptors on mammalian phagocytic cells.

Because the heptaglucoside is in an aqueous solution and by the law of mass action interacts with the cell surface, if the cell surface includes the β-glucan receptors, the cell is triggered.

The method described by the present invention for activating the β-glucan receptors with the derivatized heptaglucoside of the present invention will be equally applicable for increasing the potency of any pharmacologically active polysaccharide.

By the term "pharmacologically active" polysaccharide is meant able to interact with a biologic system to effect a biologic response.

The present invention also includes a method of enhancing an immune response to an antigen in a subject comprising administration of an amount of the heptaglucoside of the present invention to said subject in an amount sufficient to enhance the immune response of said subject to said antigen. In order to do this, the heptaglucoside of the present invention may be linked to an immunogenic carrier if necessary. Methods of accomplishing this are known to those of skill in the art.

The term "subject" means any mammal which can elicit an immune response.

The adjuvant activity of the heptaglucosides may be determined by any of a number of methods known to those of ordinary skill in the art. For example, the increase in titer of antibody against a specific antigen upon administration of the adjuvant may be used as a criteria for adjuvant activity (Dalsgaard, K. *Acta Veterinia Scandinavica* 69:1-40 (1978); Scott, M.T. et al., *Int. Archs. Allergy Appl. Immun.* 77:409-412 (1985)).

Immune adjuvant activity may also be tested by measuring the ability of the heptaglucoside of the present invention to phagocytize, secrete lysosomal enzymes, synthesize leukotrienes, and produce cytokines, among other things, thus indicating an enhanced immune response to exogenously administered antigens. The heptaglucoside of the present invention demonstrates adjuvant effects at lower doses than crude extracts. The heptaglucoside exhibits adjuvant effects when administered over a wide range of dosages and a wide range of ratios to the antigen being administered.

In one embodiment, the heptaglucoside dosage useful in the present invention to induce phagocytic cell activation in vivo in order to potentiate an immune or defense response may range from .1 ng/kg to 10 g/kg of subject weight.

The heptaglucoside of the present invention may be administered either individually or admixed with other adjuvants to achieve the enhancement of the immune response to an antigen. This heptaglucoside may also be administered together with non-heptaglucoside adjuvants. Such non-heptaglucoside adjuvants useful with the present invention are oil adjuvants (for example, Freund's Complete and Incomplete (except in humans)), liposomes, mineral salts (for example, AlK(SO$_4$)$_2$, AlNa(SO$_4$)$_2$, AlNH$_4$(SO$_4$), silica, alum, Al(OH)$_3$, Ca$_3$(PO$_4$)$_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus Brucella). Preferred non-heptaglucoside adjuvants include silica and alum.

The heptaglucoside of the present invention may be utilized to enhance the immune response to any antigen. Typical antigens suitable for the immune-response provoking compositions of the present invention include antigens derived from any microbe, including the following: viruses, such as influenza, rabies, measles, hepatitis B, hoof and mouth disease, or HTLV-III; bacteria, such as anthrax, diphtheria or tuberculosis; protozoans, such as *Babeosis bovis* or Plasmodium: fungi, yeast, helminths, other parasites, or any other substance which invokes a host defense or immune response, or would invoke such a response if administered in sufficient quantity, including aged or damaged tissue cells.

By the term "microbe" or "microbial" is meant bacteria, viruses, fungi, rickettsia, borrelia, and parasites such as helminths and protozoans.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered, and are generally described above.

The effective compound useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

The teaching of the present invention contemplates the use of the heptaglucoside in vaccine preparations. Methods of preparing vaccines are well known in the art. For example, in a vaccine developed using the teaching of the present invention, an aqueous solution of the infectious organism, preferably buffered at physiological pH, can be used directly. Alternatively, the heptaglucoside can be encapsulated within microparticles such as liposomes. It is also possible to use combinations of various infectious organisms in one vaccine.

The amount of antigen present in each vaccine dose is selected as an amount which induces an immunoprotective response without significant, adverse side effects in typical vaccines. Such amount will vary depending upon which specific antigen is employed and to what extent the vaccine is further adjuvanted. An optimal amount for a particular vaccine can be ascertained by standard studies involving observation of antibody titres and other responses in subjects well known to those of skill in the art.

Vaccines which may be prepared in conjunction with the teaching of the present invention may be formulated in conventional manner, e.g., with sterile physiologically compatible carriers such as saline solution, excipients, other adjuvants, preservatives, stabilizers, and the like. Injectable preparations will normally be formulated to be substantially isotonic. Vaccines may be in liquid form, or may be in dry form for dissolution in a sterile carrier prior to use. Vaccines may be single-dose preparations, or may be in other forms such as multidose flasks for use in mass vaccination programs. Preparations effective by subcutaneous administration will often be preferred on account of their ease of use, although other administration routes such as intravenous, intramuscular and intradermal are also contemplated.

The present invention also relates to a-method of isolating LMW polysaccharides to achieve the separation of biologically active forms from chemically similar inactive forms. Fractions containing glucose polymers that have one fewer glucose unit than the biologically active heptaglucoside of the present invention are at least 500 times less active, indicating that this method can separate hexaglucosides from heptaglucosides. Fractions containing glucose polymers that contain two fewer glucose units than the biologically active heptaglucoside of the present invention are completely resolved (and inactive), indicating that pentaglucsides can be separated from hexa- and heptaglucosides by this method.

The disruption and solubilizing of LMW polysaccharides by physical means may be accomplished by sonication. Disruption of these molecules by chemical means may be accomplished by enzyme hydrolysis, particularly using β-glucosidases, without being limiting, or preferably, limited acid hydrolysis, using, for example, trifluoroacetic acid, as described. Modifications and alternatives to the above, useful in the present invention, will be clear to the artisan of ordinary skill.

The solubilized polysaccharides may then be subjected to chromatographic fractionation in order to obtain the smallest biologically active polysaccharide capable of interacting with β-glucan receptors, as described above. Preferred chromatographic fractionation steps useful in the present invention include subjecting the solubilized product to a Bio-Gel P-4 column and collecting those products with the lowest molecular weights which exhibit biological activity. These collected products may then be subjected to a Bio-Gel P-2 column, twice, and similar fractions collected. An active heptaglucoside with an approximate molecular weight of approximately 1,000 daltons may be obtained at this point.

The chromatographically fractionated biologically active heptaglucoside fraction may then be derivatized. Derivatization of the fractionated product with 2-aminopyridine is one of the key steps discovered by the inventors to permit the separation of LMW polysaccharides from one another, as well as to stimulate and potentiate the activity of β-glucan receptors. By this procedure, one molecule of 2-aminopyridine is introduced and fixed to one sugar unit in each of the solubilized polysaccharides. On a weight basis, derivatization increases the efficiency at which the biologically active polysaccharides interact with the β-glucan receptors by about 70-fold, but does not confer activity to inactive polysaccharides.

The derivatized fraction may then be subjected to a further chromatographic fractionation step, resolved, for example, by normalphase high performance liquid chromatography (HPLC). Only one of several collectable fractions will have biological activity, and this fraction includes the heptaglucoside described by the present invention. It is clear, however, that other fractionation procedures may be used to isolate LMW poysaccharides from one another, and specifically, to isolate the heptaglucoside of the present invention.

This method permits isolation of the smallest functional glucose polymer that interacts with the β-glucan receptors. This heptaglucoside has its seven glucose units spatially arranged in a specific way. Its molecular weight is approximately 1,000. Less than one-billionth of a gram (nanogram) of the isolated derivatized heptaglucoside is required for biologic function. In terms of weight, the active heptaglucoside is 40,000 times more active than the unfractionated mixture of solubilized polysaccharides in interacting with human monocyte β-glucan receptors, and 1,000 times more active than any other compound thus far described with such a function. This derivatized yeast heptaglucoside is therefore of immense interest as an active pharmacologic agent for receptors that have important biologic functions.

EXAMPLES

Having now fully described the present invention, the same will be more clearly understood by reference to certain specific examples which are included herewith for purposes of illustration only and are not intended to be limiting of the invention, unless specified.

ABBREVIATIONS

BSA: bovine serum albumin; $E^{s}$IgG: IgG-coated sheep erythrocytes; FAB: fast-atom-bombardment; GC: gas chromatography; HBSS: Hanks' balanced salt solution, pH 7.4, lacking phenol red, calcium, and magnesium; HPLC: high-performance liquid chromatography; RPMI-Mg: RPMI 1640 medium containing 5 mM $MgCl_2$; RPMI-Mg-HEPES: RPMI 1640 medium containing 5 mM $MgCl_2$ and 10 mM 4-(2-hydroxyethyl)-1- piperazinecontaining ethane-sulfonic acid; TFA: trifluoroacetic acid.

EXAMPLE I

Quantitation of Hexose and Protein in Glucan Preparations

The amount of carbohydrate was determined in terms of hexose equivalents by the anthrone method (Dische, Z., General Color reactions, in *Methods in Carbohydrate Chemistry* (Whistler, R.C., and Wolfrom, M.L., eds.) pp. 478–512, Academic Press, New York (1962)) with glucose standards for calibration. The amount of protein was determined by the Lowry method (Lowry, O.H. et al., *J. Biol. Chem.* 193:265 (1951)) with BSA as the reference standard. To determine neutral sugar compositions, samples were derivatized to alditol acetates (Schmid, K. et al., Prep. Biochem. 6:27 (1976)) and analyzed by GC (Janusz, M.J. et al., *J. Immunol.* 37:3270 (986)).

EXAMPLE II

Assessment of Phagocytosis by Adherent Monocytes

Normal human mononuclear cells were isolated from citrated blood by dextran sedimentation of erythrocytes, washed free of plasma and platelets in HBSS, and purified by gradient centrifugation (Boyum, A., *Scand. J. Clin. Lab. Invest.* 21(Suppl. 91):31 (1968)) on Ficoll-Hypaque (Pharmacia Fine Chemicals, Piscataway, NJ) cushions. The mononuclear cells were washed in HBSS, resuspended in RPMI 1640 medium (GIBCO, Grand Island, NY) that had been supplemented with 0.1% BSA (crystallized, Miles Laboratories Inc., Elkhart, IN), and counted on a Coulter counter.

Monolayers of monocytes, prepared on siliconized glass coverslips (Czop, J.K. et al., *J. Immunol.* 120:1132 (1978)), were pretreated for 15 min in a humidified 5% $CO_2$ chamber at 37° C. with 0.25 ml of various concentrations of isolated yeast carbohydrates in RPMI-Mg, pH 7.4 and RPMI-Mg-HEPES. They were then washed twice in 50-ml volumes of RPMI 1640 medium and layered with 0.25 ml of $5 \times 10^6$/ml zymosan particles (Czop, J.K. et al., *J. Immunol.* 134:2588 (1985)) or $1 \times 10^7$/ml $E^sIgG$ (Czop, J.K. et al., ibid.) in RPMI-Mg.

After incubation for 30 min at 37° C., the monolayers were rinsed in three 50-ml volumes of HBSS, treated for 4 min with 0.84% $NH_4Cl$ to lyse uningested $E^sIgG$, fixed (Czop, J.K. et al., *J. Immunol.* 120:1132 (1978)), and stained with Giemsa. The number of particles ingested by at least 300 monocytes per monolayer was determined by visual enumeration at $1000\times$ with a light microscope, and the percentages of monocytes ingesting $\geq 1$ and $\geq 3$ targets were calculated.

The data are expressed as percent inhibition, which was determined by dividing the percentage of monocytes ingesting targets after pretreatment with isolated carbohydrates by the percentage ingesting targets after pretreatment with buffer, subtracting this ratio from 1, and multiplying the remainder by 100. The percentages of monocytes ingesting targets after pretreatment with buffer are included for each experiment (see figures and text).

EXAMPLE III

Purification and Partial Acid Hydrolysis of Yeast Glucan Particles

Alkali-insoluble glucan particles were prepared from *S. cerevisiae* (Fleischmann, E. Hanover, NJ) as described (Manners, D.J. et al., *J. Gen. Microbiol.* 80:411 (1974)) except that the final product was dried under vacuum in acetone. The glucan particles contained 96% carbohydrate and 4% protein and the only neutral sugar detected was glucose. To prepare hydrolysates, 50–100 mg of glucan particles were suspended at a concentration of 5 mg/ml in 2 M TFA, heated at 85° C. for 110 min in 25-ml reactiflasks (Pierce Chemical Co., Rockford, IL), cooled, and centrifuged at $160\times$ g for 10 min at 25° C. Supernatant fractions from 10 reactiflasks were pooled and the residual TFA was removed by rotoevaporation at 35°–40° C. in a silanized (Sharp, J.K. et al., *J. Biol. Chem.* 259:11312 (1984)) round-bottom flask. The resulting syrup was dissolved in 10 ml of distilled water, neutralized with 1 N NaOH, and brought to a concentration of 15 mg/ml hexose equivalents with distilled water.

EXAMPLE IV

Gel Filtration of Acid-Solubilized Yeast β-qlucans

A Bio-Gel P-4 column ($170 \times 2$ cm) was equilibrated in distilled water, loaded with 150 mg of acid-solubilized glucans, and eluted in distilled water at a flow rate of 28 ml/h at 10° C. Fractions of 2.9 ml were collected and assessed for hexose content and phagocytosis-inhibiting activity. Biologically active oligoglucosides with estimated $M_r$ 1000 were pooled from seven replicate column runs, lyophilized, and dissolved in distilled water to 45 mg/ml hexose equivalents. For further separation, a water-jacketed Bio-Gel P-2 column ($100 \times 1$ cm) was equilibrated in distilled water, maintained at 65° C., loaded with 18 mg of the pooled Bio-Gel P-4 materials, and eluted in distilled water. Fractions of 0.5 ml were collected at a flow rate of 15 ml/h and assessed for hexose content and phagocytosisinhibiting activity. The total carbohydrate recovered was $91 \pm 13\%$ (mean±SD, n=6) and the biologically active oligoglucosides from six columns were pooled and lyophilized.

EXAMPLE V

Derivatization and Separation of Oligoglucosides by HPLC

To permit detection of microgram quantities of carbohydrates by HPLC, oligoglucosides were derivatized by the method of Her et al. (*J. Carbohydr. Chem.* 6:129 (1987)) with 2-aminopyridine. Two milligrams of sample were heated in 50 μl of 3.5 M 2-aminopyridine in 3 M HCl for 18 h at 65° C. Normal-phase HPLC of 200 μg of derivatized oligoglucosides was carried out on a 5 μm-Spherisorb amino column ($250 \times 4.6$ mm; Phase Separations, Clwyd, UK) fitted with an amino guard cartridge (Brownlee Laboratories, Santa Clara, CA) and the sample eluted in a linear gradient of 80% to 50% acetonitrile in water (v/v) at a flow rate of 1 ml/min. Absorbance at 232 nm ($A_{232}$) of the column eluate was continuously monitored with an on-line spectrophotometer (Model 116, Gilson Medical Elec., Inc., Middleton, WI) and fractions of 1 ml were collected into silanized glass tubes and lyophilized. To determine carbohydrate content, samples, dissolved in distilled water, were analyzed in known volumes by GC and quantitated by integration with the internal standard m-inositol for calibration.

It should be noted that no step which is a part of the method of this invention affects the biologic activity of a derivatized oligoglucoside differently from a nonderivatized oligoglucoside. Therefore, the stage at which derivatization is carried out is irrelevant.

EXAMPLE VI

FAB-Mass Spectrometry

Two micrograms of sample derivatized with 2-aminopyridine were analyzed by FAB-mass spectrometry by Dr. Guor Rong Her, Harvard School of Public Health, Boston, as described (Her, G.R. et al., *J. Carbohydr. Chem.* 6:129 (1987)).

EXAMPLE VII

Separation of Yeast Oligoglucosides with Phagocytosis-Inhibiting Activity by Gel Filtration Seven batches of purified yeast glucan particles were subjected to partial acid hydrolysis to prepare solubilized products, which contained 23±4% (mean±SD, n32 7) of the total carbohydrate in glucan particles. Each of the seven solubilized products was separately fractionated by gel filtration on a Bio-Gel P-4 column and the eluted samples were assessed for hexose content and for effects on monocyte ingestion of zymosan particles.

As depicted for one chromatogram of solubilized material (FIG. 1), partial acid hydrolysis of glucan particles yielded glucose molecules and oligoglucosides that were heterogeneous in size and inhibited monocyte ingestion of zymosan. Pretreatment of monocytes with eluted fractions containing 50 µg/ml of carbohydrate revealed nearly equal levels of phagocytosis-inhibiting activity by oligoglucosides eluting within the inclusion volume of the column.

To isolate the smallest ligand unit recognized by monocyte β-glucan receptors, pooled samples containing oligoglucosides with estimated $M_r$ 1000 and accounting for 10±2% (mean±SD, n=7) of the applied acid-solubilized carbohydrates were gel-filtered on a Bio-Gel P-2 column, and the eluted fractions were assessed for hexose content and phagocytosis-inhibiting activity. As shown with a representative chromatogram in FIG. 2, the eluted oligoglucosides were again heterogeneous in size but phagocytosis-inhibiting activity was present in only one peak, which, relative to oligomeric standards, contained heptoses. The biologically active material from Bio-Gel P-2 columns accounted for 8±2% (mean±SD, n=6) of the carbohydrate applied, contained 98% carbohydrate and 1.5% protein, and had no neutral sugar other than glucose. The FAB-mass spectra of this material showed it to be a mixture of penta-, hexa, and heptaglucosides.

To compare the phagocytosis-inhibiting activity of acid-solubilized yeast carbohydrates in unfractionated and fractionated samples, monocytes were pretreated with increasing concentrations of the carbohydrates in acid-solubilized total hydrolysates and with the oligoglucosides filtering with estimated $M_r$ 1000 on Bio-Gel P-4 and Bio-Gel P-2, and were assessed for their capacities to ingest zymosan particles (FIG. 3). A 50% reduction in the number of monocytes injesting zymosan particles occurred with about 75 µg/ml of the total hydrolysate and a plateau of approximately 85% reduction was obtained with 200 µg/ml. Initial plateau inhibitory levels of 45±1% and 42±7% (mean±SD, n=3) were effected with 0.5 µg/ml of the carbohydrates eluted as $M_r$ 1000 oligoglucosides from Bio-Gel P-4 and P-2, respectively; inhibition increased to about 55% with 50 µg/ml of either sample.

EXAMPLE VIII

Figure 4:
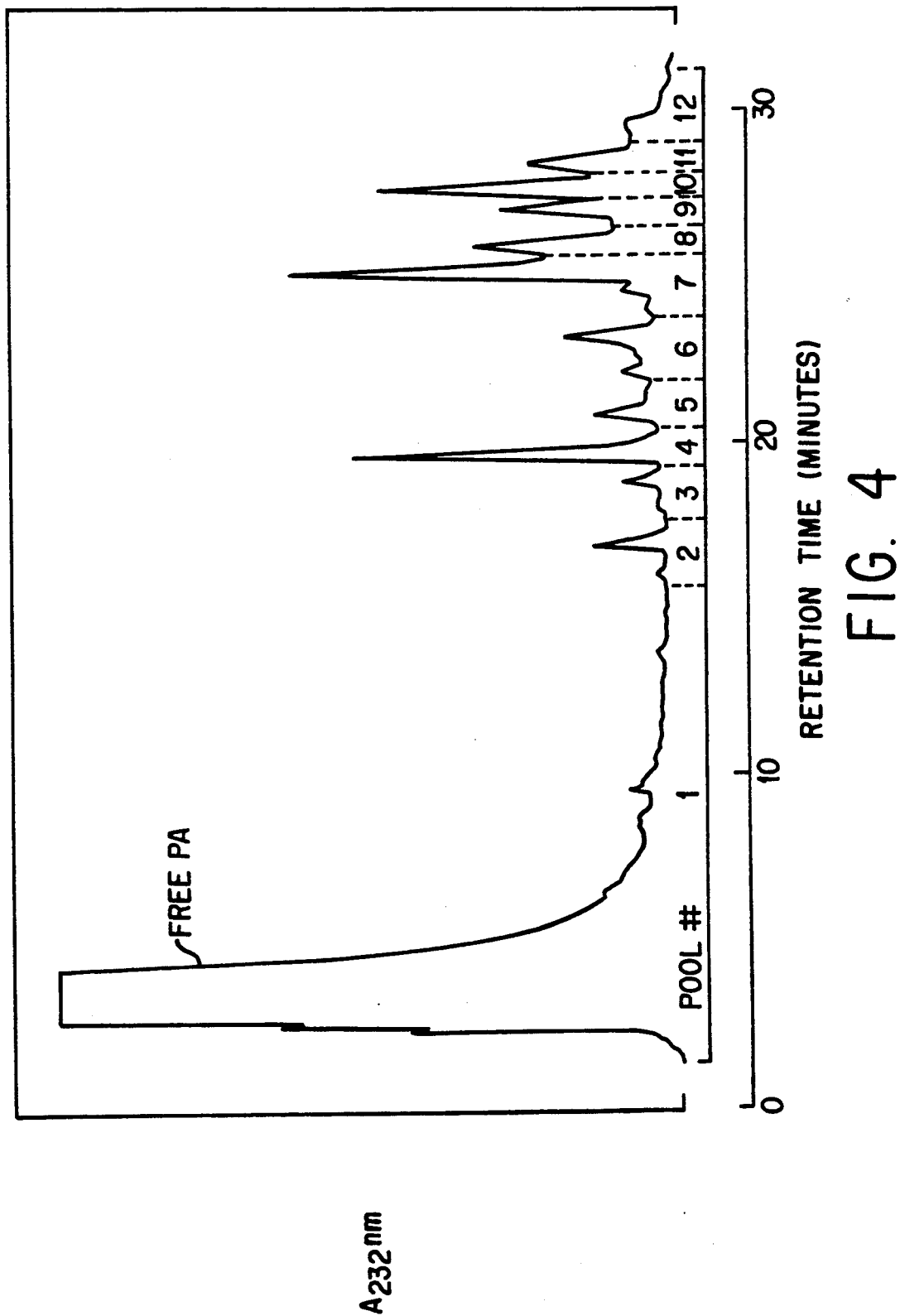
FIG. 4. Normal-phase HPLC of 2-aminopyridine (PA) derivatives of the biologically active oligoglucosides in Bio-Gel P-2 pooled materials. Absorbance at 232 nm (----) was determined in 1-ml eluted fractions. Twelve pools of the eluted samples were prepared as designated.

Purification of Yeast Heptaglucosides with Phagocytosis-Inhibiting Activity by HPLC The biologically active oligoglucosides obtained from the Bio-Gel P-2 columns were derivatized with 2-aminopyridine and resolved by normal-phase HPLC (FIG. 4). Based on optical density peaks, twelve fractions were prepared and each was assessed at a concentration of 800 ng/ml for its capacity to suppress monocyte ingestion of zymosan particles. Materials eluting with retention times of <26.5 min (pools 1-7), and >29.5 min (pool 12), had no effect on monocyte ingestion of zymosan particles, whereas materials in pools 8-11 were inhibitory (data not shown).

Figure 5:
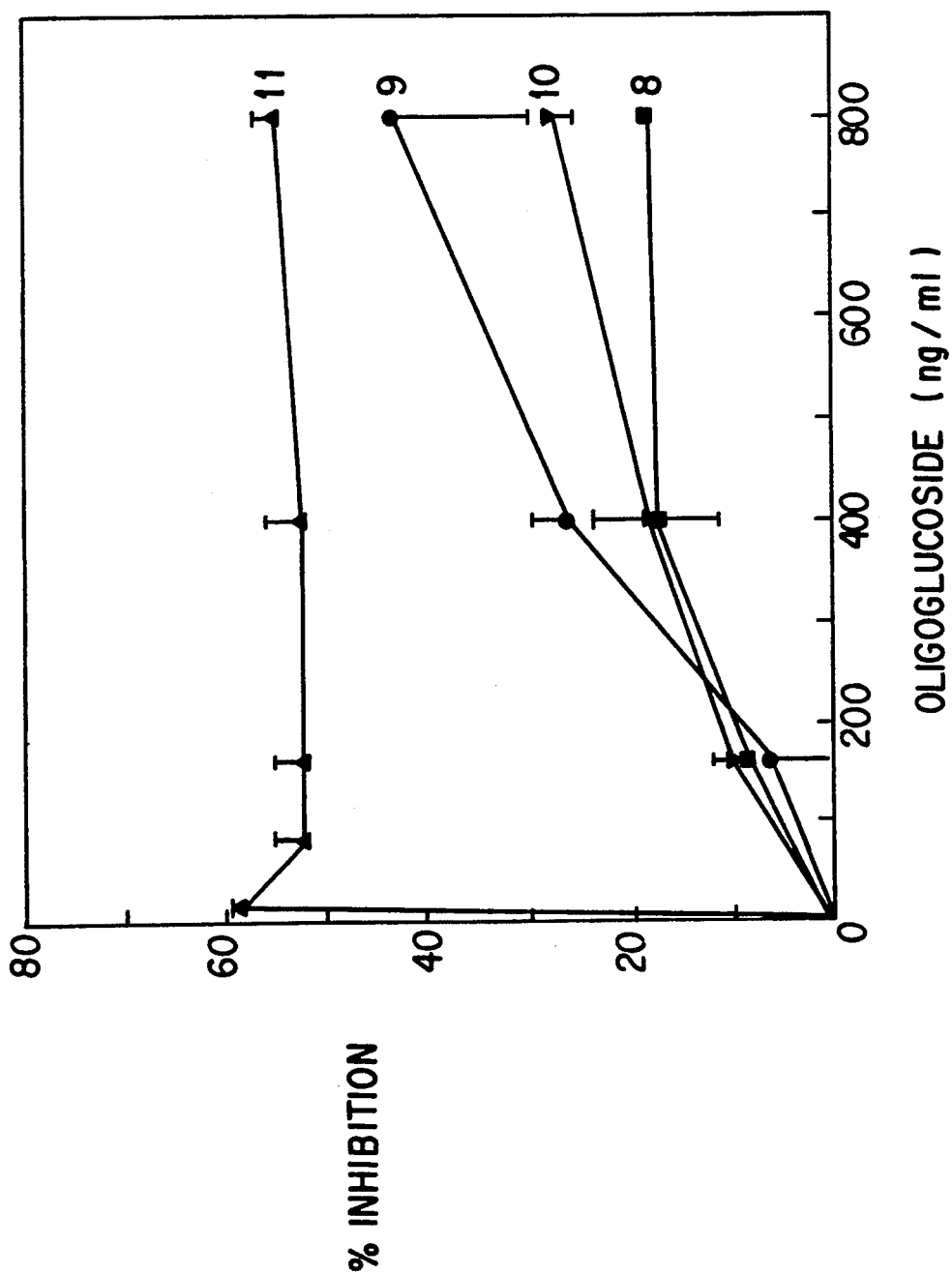
FIG. 5. Dose-dependent effects of pretreatment of monocytes with HPLC-purified oligoglucosides in pools 8 (□), 9 (0), 10 (▽), and 11 (△) on subsequent monocyte ingestion of zymosan particles. The data are expressed as percent inhibition and are plotted as the mean with range from two experiments. In the absence of test materials, the percentages of monocytes ingesting zymosan particles were 44% and 66%.

To compare the levels of phagocytosis-inhibiting activity in pools 8-11, monocytes were pretreated with 16-800 ng/ml of each pool and were then assessed for their ingestion of zymosan particles (FIG. 5). Materials in pools 8-10 inhibited monocyte ingestion of zymosan in a dose-related fashion, reaching about 20-30% suppression at a concentration of 400 ng/ml; pool 11 effected plateau inhibitory levels of 58% at a concentration of only 16 ng/ml. At concentrations as high as 800 ng/ml, the material in pool 11 had no effect on the proportion of monocytes ingesting E$^s$IgG, which averaged 78% after pretreatment of monocytes with buffer or oligosaccharide.

Figure 6A:
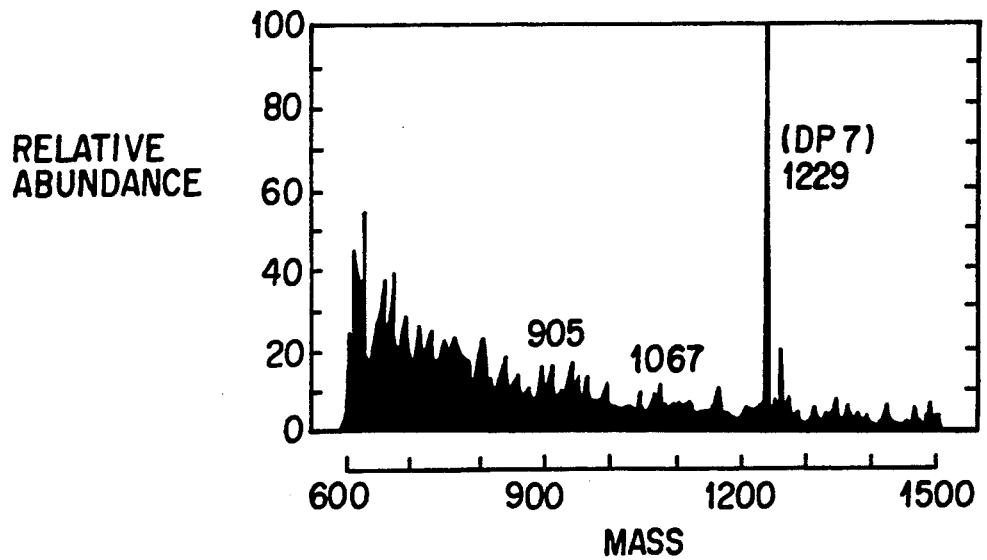
FIG. 6. FAB-mass spectra of HPLC-purified oligoglucosides in pools 11 (A), 10 (B), 9 (C), and 4 (D). The data are given as the relative abundance of mass with the mass number and the degree of polymerization (DP) indicated.
Figure 6B:
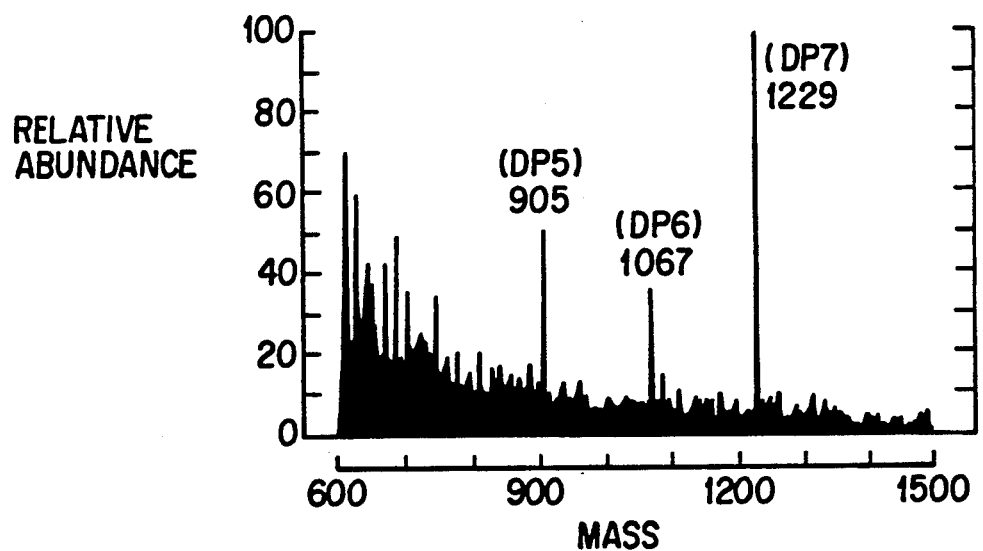
Figure 6C:
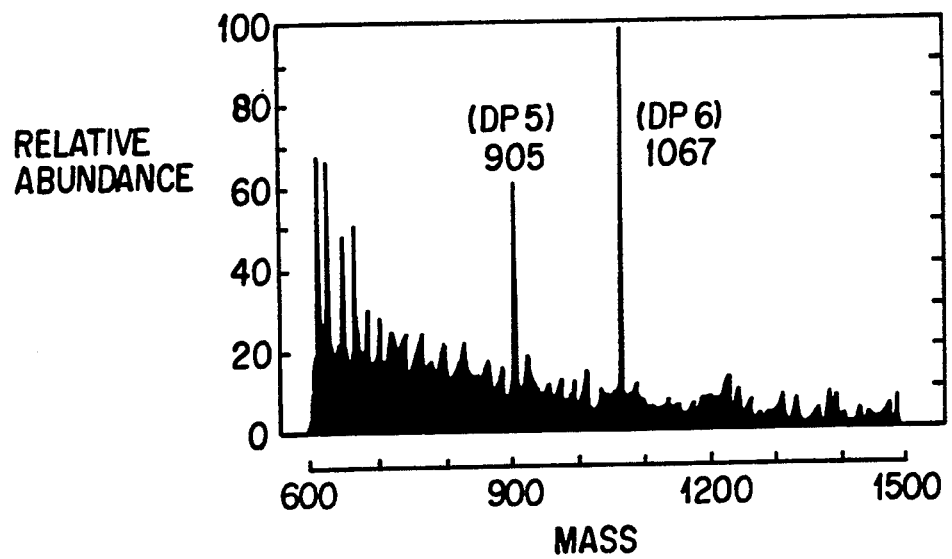

In seven HPLC fractionations, the material in pool 11 contained 8.8±0.9% (mean±SD) of the derivatized oligoglucosides applied, 6.6 ±0.7% of the carbohydrate applied, and 62% of the phagocytosis-inhibiting activity applied. GC analysis of pool 11 revealed only inhibiting activity glucose and FAB-mass spectrometric analysis showed only heptaglucoside and no non-carbohydrate molecules (FIG. 6A). The FAB-mass spectra of the material in pool 10 identified it as a mixture of penta-, hexa-, and heptaglucosides (FIG. 6B), and that in pool 9 as a mixture of penta- and hexaglucosides (FIG. 6C).

Figure 7:
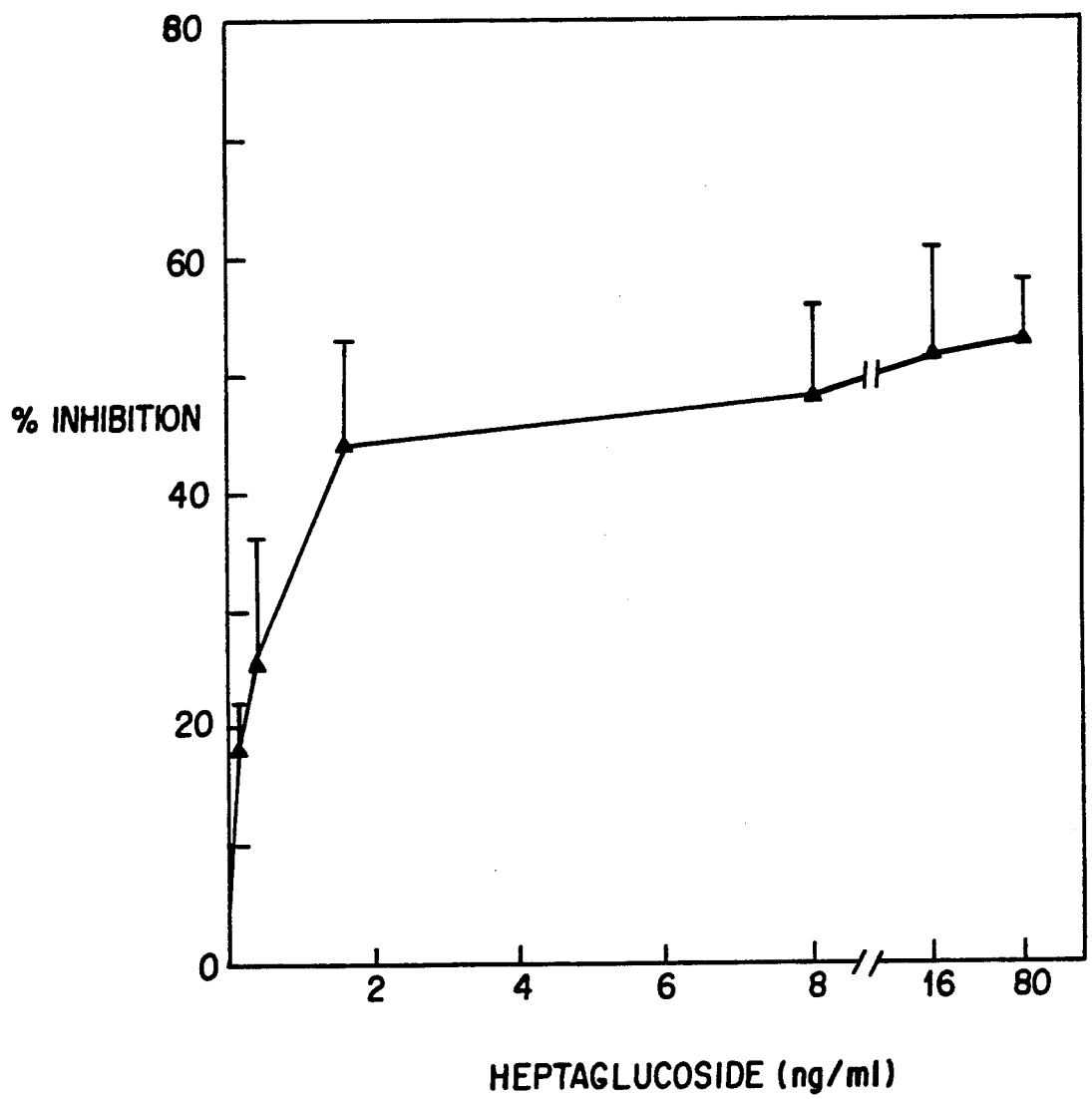
FIG. 7. Dose-dependent effects of pretreatment of monocytes with the HPLC-purified yeast heptaglucoside in pool 11 on subsequent monocyte phagocytosis of zymosan particles. The data are expressed as percent inhibition and are plotted as the mean±SD, n=5. For cells pretreated with buffer alone, the percentage of ingesting monocytes was 55±10%.

To determine the specific activity of the HPLC-purified yeast heptaglucoside, monocytes were pretreated with 0.16 to 80 ng/ml of the heptaglucoside and assessed for their ingestion of zymosan particles (FIG. 7). The percentage of monocytes ingesting zymosan, initially 55 ±10% (mean±SD, n=5) for cells pretreated with buffer alone, was reduced in a dose-dependent fashion to plateau inhibitory levels of 44 ±9% by 1.6 ng/ml of the heptaglucoside. At a 10-fold higher concentration, the yeast heptaglucoside reduced monocyte ingestion of zymosan particles by 52±9% and this value represented a maximal effect that was unchanged by as much as 80 ng/ml of the heptaglucoside.

EXAMPLE IX

Comparison of Effect of Derivatization on Biologic Activity of Other Molecules Maltoheptose, a linear α-D-glucan with 1,4 linkages, and a synthetic β-heptaglucoside with elicitor activity (Sharp, J.K. et al., *J. Biol. Chem.* 259:11341 (1984)), a branched β-D-glucan with consecutive 1,6 and interchain 1,3 linkages, were derivatized with 2-aminopyridine and resolved by HPCL. Maltoheptose and the synthetic β-heptaglucoside eluted with retention times of 28.2 and 31.5 min, respectively, which compared to 29.1 min for the yeast heptaglucoside pool 11 (data not shown).

To determine if either of these molecules exhibited phagocytosisinhibiting activity, two overlapping dose-response experiments were carried out with the synthetic β-heptaglucoside and three with maltoheptose, each without derivatization. At inputs ranging from 50 ng/ml to 100 μg/ml, the synthetic β-heptaglucoside had no effect on monocyte ingestion of zymosan particles; the average proportions of monocytes ingesting zymosan with and without pretreatment with 100 μg/ml of the synthetic β-heptaglucoside were 71% and 67%, respectively (data not shown).

Maltoheptose, at concentrations ranging from 500 ng/ml to 100 μg/ml, had no effect on monocyte ingestion of zymosan. The proportions of monocytes ingesting zymosan with and without pretreatment with 100 μg/ml were 52% and 50% respectively (data not shown). Phagocytosis-inhibiting activity was not acquired by the synthetic β-heptaglucoside or maltoheptose after derivatization with 2-aminopyridine when 100 ng/ml were tested.

EXAMPLE X

Unanticipated Enhanced Biologic Potency of Heptaglucosides

In this example, yeast glucan particles were purified from Fleischmann's yeast. To prepare soluble glucans, one gram of the glucan particles was rehydrated in water, heated at 85° C. for 2 hr in 2 N TFA, and subjected to centrifugation, as described, to separate the soluble and insoluble products. The soluble materials were removed, concentrated by lyophilization, neutralized with 1 N NaOH, and assessed for carbohydrate content and biologic activity with human monocyte β-glucan receptors.

For seven separate batches of particulate glucan, partial acid hydrolysis solubilized 23±4% (mean±SD, n=7) of the yeast cell wall glucan. In biological assays with monocytes, 50 μg/ml of the unfractionated acid soluble products were required to effect a 50% reduction in monocyte ingestion of the particulate yeast cell wall product zymosan.

The acid solubilized glucans were gel-filtered on a Bio-Gel P-4 column and the eluted fractions assessed for carbohydrate content and biologic activity. Gel-filtration of the soluble glucans on this column revealed that partial acid hydrolysis yielded a mixture of LMW oligoglucosides as well as glucose molecules. Biologic activity was limited to several well-defined peak areas containing oligoglucosides of different molecular weights.

One of these active moieties was selected for further purification, namely that which contained the lowest molecular weight oligoglucoside. This material had an estimated molecular weight of 1000 and accounted for 10±2% (mean±SD, n=7) of the total carbohydrate applied. Fractions containing this moiety were pooled and subjected to further purification on a Bio-Gel P-2 column. This resolved the biologic activity to a single peak that contained an apparent heptamer of glucose and accounted for 8% of the carbohydrate applied. On a weight basis, the active carbohydrates before and after resolution on Bio-Gel P-2 were 100-fold more effective in interacting with monocyte β-glucan receptors than the unfractionated soluble glucans (Table 1).

TABLE 1

PURIFICATION OF HPLC-YEAST HEPTAGLUCOSIDE WITH BIOLOGIC ACTIVITY FOR HUMAN MONOCYTE β-GLUCAN RECEPTORS

| Sample | Yield[1] mg | Biological acivity units/μg[2] | Increase in activity |
|---|---|---|---|
| Acid solubilized products | 230.00 | 0.02 | 1 |
| Bio-Gel P-4 pool[3] | 23.00 | 2.00 | 100 |
| Bio-Gel P-2 pool | 1.84 | 2.00 | 100 |
| Derivatized HPLC-heptaglucoside | 0.12 | 625.00 | 31,250 |

[1]Amount of carbohydrate (glucose equivalents) per gram of purified particulate yeast glucan.
[2]One unit is the amount of carbohydrate required to reduce the numbers of human monocytes ingesting $5 \times 10^6$/ml zymosan particles by 50%
[3]These data are for the smallest biological active oligoglucosides eluted from this column.

The active materials from the Bio-Gel P-2 column were pooled and derivatized with 2-aminopyridine by the dehydration reaction described by Her et al. (J. Carbohydr. Che. 6:129 (1987)). Two milligrams of sample were heated in 50 μl of 3.5 M 2-aminopyridine in 3 M HCl for 18 hr at 65° C. The derivatized oligoglucosides were applied to an amino-HPLC column and eluted in a linear gradient of 80% to 50% acetonitrile in water (vol/vol) at a flow rate of 1 ml/min. Absorbance at 232 nm of the column eluate was continuously monitored with an on-line spectrophotometer and fractions of 1 ml were collected.

HPLC-separation of the derivatized oligoglucosides yielded 10-12 carbohydrate-containing peak fractions. A peak that eluted as an apparent heptaglucoside contained virtually all of the biologic activity for monocyte β-glucan receptors and accounted for 6.6% of the carbohydrate applied. Compositional analysis of this fraction by GC revealed only glucose, and mass analysis by FAB spectrometry showed only heptaglucoside and no non-carbohydrate molecules. Derivatized yeast penta- and hexaglucosides, as well as heptaglucosides in other HPLC-peaks, failed to interact with monocyte β-glucan receptors. On a weight basis, the derivatized yeast heptaglucoside was, on average, 31,250 times more active in being recognized by monocyte β-glucan receptors than the unfractionated acid-soluble yeast glucans (Table 1).

EXAMPLE XI

Direct Comparison of Oligoglucosides With and Without Derivatization with 2-aminopyridine Since the HPLC-purified yeast heptaglucoside had more activity than the inventors expected, the effect of derivatization on subsequent biologic activity was examined. Active carbohydrates obtained from sequential Bio-Gel P-4 and P-2 columns were derivatized with 2-aminopyridine as described above and a portion was subjected to HPLC chromatography.

To compare biologic activity, dose response experiments were carried out in the monocyte assay with the HPLC-purified yeast heptaglucoside, its derivatized Bio-Gel P-2 starting material, and the same Bio-Gel P-2 pool that had not been derivatized with 2-aminopyridine. The results of this experiment are given in Table 2.

TABLE 2
EFFECT OF DERIVATIZATION WITH 2-AMINOPYRIDINE OF YEAST OLIGOGLUCOSIDES WITH BIOLOGIC ACTIVITY FOR MONOCYTE β-GLUCAN RECEPTORS

| Sample | Derivatized with 2-aminopyridine | Actual Activity[1] (ng/ml) | Anticipated Activity[2] (ng/ml) |
|---|---|---|---|
| Bio-Gel P-2 pool | no | 520.0 | 500 |
| Bio-Gel P-2 pool | yes | 6.4 | 500 |
| HPLC-heptaglucoside | yes | 0.6 | 42 |

[1]Concentration of carbohydrate required to reduce the numbers of human monocytes ingesting zymosan particles by 50%.
[2]The anticipated activity is the concentration of carbohydrate expected to be required to reduce monocyte ingestion of zymosan by 50%. The value for the active Bio-Gel P-2 was not expected to change after derivatization with 2-aminopyridine. The amount of activity anticipated for the HPLC-purified heptaglucoside is based on the resolution of the Bio-Gel P-2 mixture to 10–12 HPLC-separable carbohydrate constituents. As indicated, the actual activity of the derivatized HPLC-isolated heptaglucoside was 70-fold greater than expected.

Derivatization alone, without subsequent HPLC separation, increased the activity of the Bio-Gel P-2 fractionated materials 80-fold. A further 9-fold increase in activity was achieved by HPLC separation of the active heptaglucoside from this mixture. Thus, the derivatization procedure not only provided a method for monitoring carbohydrate molecules but also increased the potency of the heptaglucoside for mammalian phagocytic cell β-glucan receptors.

It is to be noted that two heptaglucosides, namely maltoheptose and the fungal β-heptaglucoside isolated by Sharp et al. (J. Biol. Chem. 259:11312 (1984)), remained inactive after derivatization with 2-aminopyridine (see Example IX). For these assessments, as much as 800 ng/ml of the derivatized materials were used in the functional monocyte assays. Thus, 2-aminopyridine did not confer activity to inactive carbohydrate molecules.

SUMMARY

Figure 2:
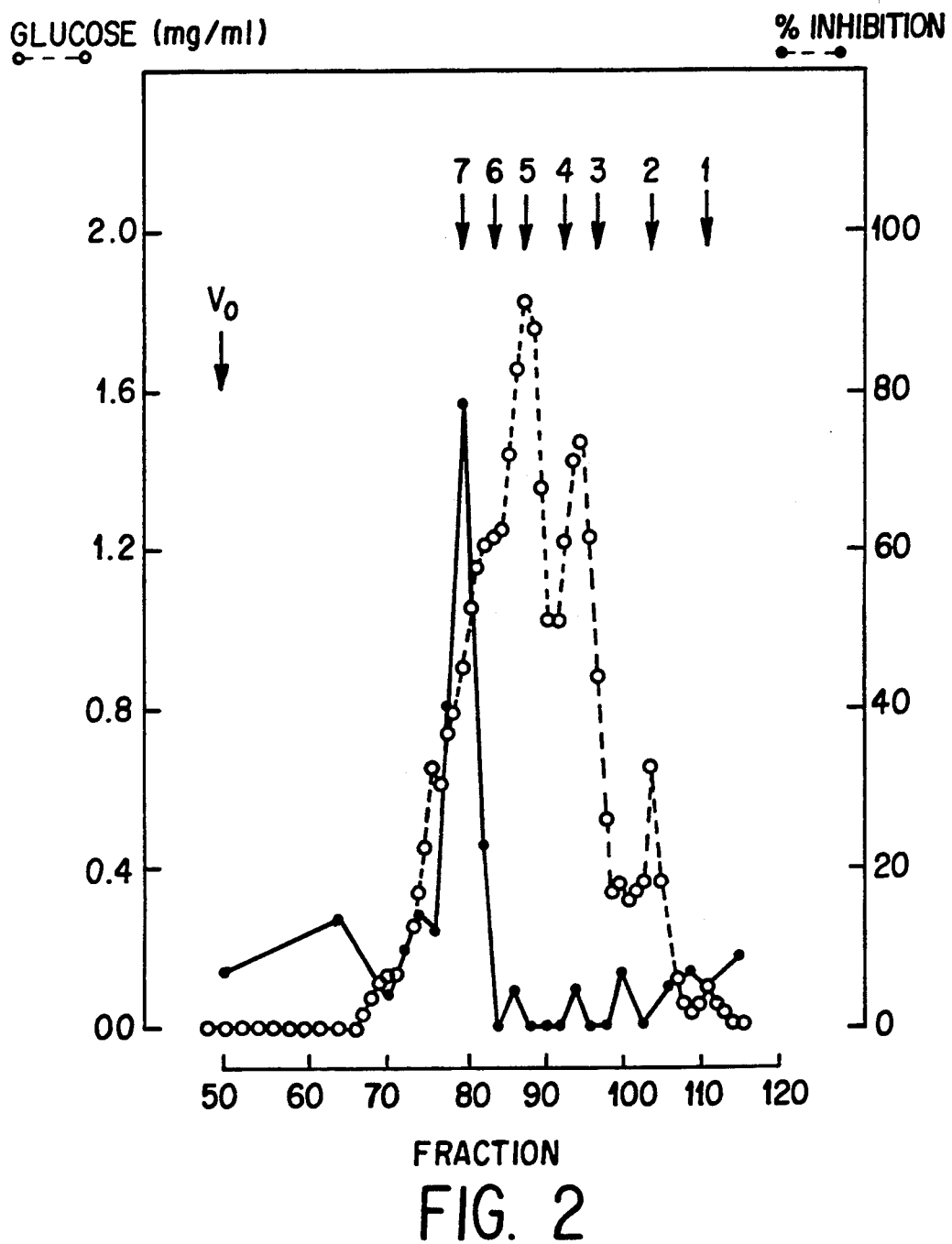
FIG. 2. Filtration of the pooled Bio-Gel P-4 fractions on Bio-Gel P-2. Fractions were assessed for glucose content (o---o) and for effects on monocyte phagocytosis of zymosan particles (●---●). The positions of the void volume ($V_o$) and the eluting peaks of the standards glucose and oligomers of maltose with the designated number of glucosyl residues are indicated. The percentage of monocytes ingesting zymosan after preincubation with buffer alone with 56% and the sample fractions were tested at a concentration of 50 μg/ml of hexose equivalents.

The initial step of gel-filtering acid-solubilized yeast glucans on Bio-Gel P-4 revealed that the smallest oligoglucosides with phagocytosis-inhibiting activity were similar in size to heptoses (FIG. 1) and these were more sharply resolved by filtration on Bio-Gel P-2 (FIG. 2). The specific activities of the materials eluted before and after fractionation on Bio-Gel P-2 were similar (FIG. 3B, C), even though about 90% of the carbohydrates had been removed from the pooled fractions by sequential chromatography. Such a lack of correspondence between increased purity and specific activities is also exhibited by the plant-inducing fungal oligoglucosides obtained by sequential low-and high-resolution gel filtration (Sharp, J.K. et al., J. Biol. Chem. 259:11312 (1984)).

Figure 6D:
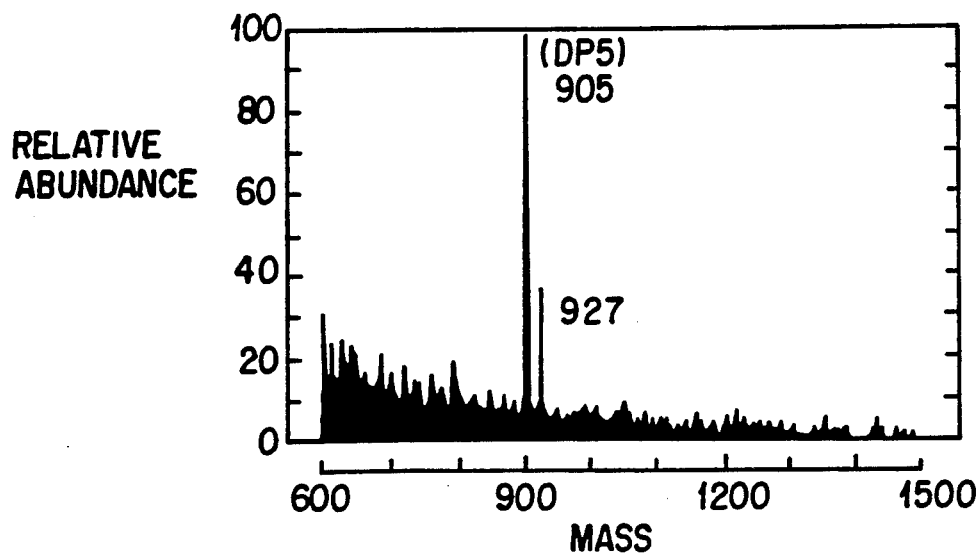

Derivatization of the pooled Bio-Gel P-2 oligoglucosides with 2-aminopyridine increased the phagocytosis-inhibiting activity of these materials by about 70-fold. Derivatized maltoheptose and the synthetic β-heptaglucoside remained inactive. HPLC-separation of the mixtures of oligoglucosides in the peak from Bio-Gel P-2 filtration yielded molecules of different sizes (FIG. 4) and different specific activities (FIG. 5). Phagocytosis-inhibiting activity was not exhibited by the pentaglucosides (FIG. 6D) in pool 4, but was expressed by the penta- and/or hexaglucosides (FIG. 6C) in pool 9 (FIG. 5). The inhibitory capacities of the materials in pools 8, 9 or 10, however, were 2–3 logs less than that of the purified yeast heptaglucoside (FIG. 6A) in pool 11 (FIG. 7), indicating that a unit ligand of several glucose residues interacted most effectively with monocyte β-glucan receptors.

Figure 3A:
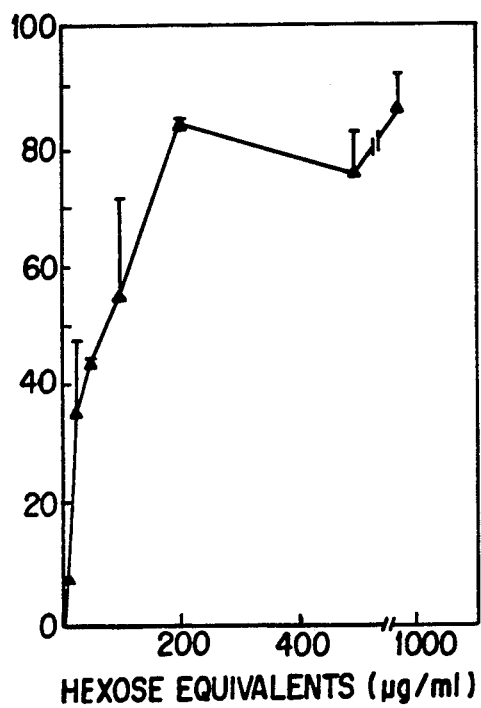
FIG. 3. Dose-dependent effects of pretreatment of monocytes with carbohydrates in acid-solubilized total hydrolysate of yeast glucan (A) and in pooled materials eluted from Bio-Gel P-4 filtration (B) and Bio-Gel P-2 filtration (C) on subsequent monocyte ingestion of zymosan particles. The data are expressed as percent inhibition and are plotted as an average with range (A) and mean±SD (B, C) of three experiments. The proportion of monocytes ingesting zymosan particles after preincubation with buffer alone was 50±9%.
Figure 3B:
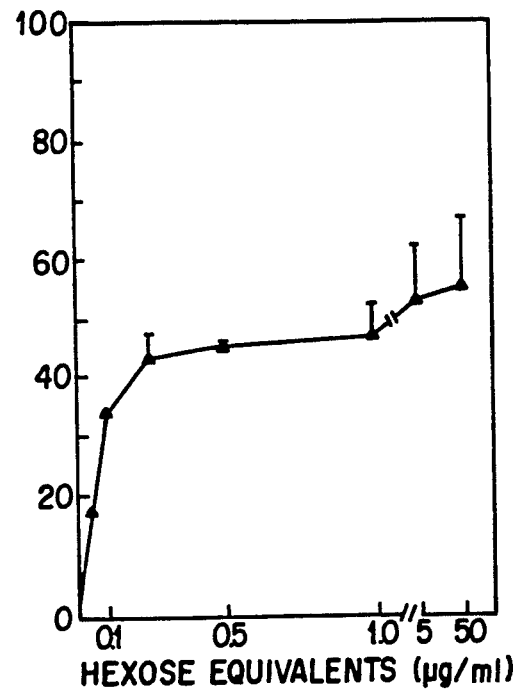
Figure 3C:
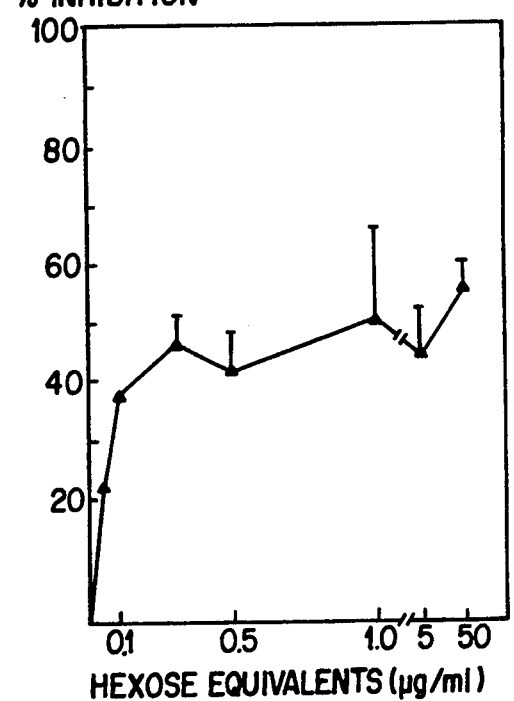

The isolation of this unit ligand was based upon selection of biologically active materials with the smallest molecular sizes and exclusion of larger and active oligoglucosides among the acid-solubilized yeast products (FIG. 1). These smaller oligosaccharides obtained after gel filtration or HPLC had maximal phagocytosis-inhibiting activities of about 50–55% (FIGS. 3B-C, 7), whereas the acid-solubilized products in total hydrolysates effected nearly full suppression of monocyte ingestion of zymosan particles (FIG. 3A).

The active heptaglucoside serving as a unit ligand for the human monocyte β-glucan receptor was shown to be functionally distinct from other structurally defined heptaglucosides, including that which elicits phytoalexin synthesis by plants.

At present, there are no reasonable methods and most assuredly there are no methods approaching this invention for isolating these types of biochemical moieties, namely complex polysaccharides. Sharp et al., J. Biol. Chem. 259:11312 (1984) and Sharp et al., J. Biol. Chem. 259:11321 (1984) have prepared and isolated LMW complex carbohydrates with biologic activity. However, their system involves plants and did not involve derivatization with 2-aminopyridine (their heptaglucoside does not interact with human mmonocyte β-glucan receptors).

In 1974, another group of plant carbohydrate chemists set out to isolate and determine the structure of the smallest fungal cell wall unit that stimulated plants to synthesize phytoalexins (Albersheim et al., J. Cell Biol. 78:627 (1978)). It seemed simple because the fungal cell wall consists of repeating units of only one sugar, glucose. The project took 10 years, and Sharp isolated less than 0.1 g of usable material. Of this, less than one-thousandth (100 μg) was of sufficient purity for structural analysis.

This prior work underscores two novel aspects of the present invention. First, the Albersheim group is considered to be a world-renowned group of carbohydrate chemists who are presumably familiar with classical chemical interactions between reducing end sugars and cyclic amines such as 2-aminopyridine.

In fact, Sharp did modify the reducing end sugar of her materials by reducing it with sodium borohydride, but this does not provide a fluorescent tag for sensitive detection. To isolate her material, she used a sensitive biological plant system and monitored for carbohydrate content by the very insensitive method of refractive index, which requires very large amounts of material. Because the resolution of the refractive index method is so poor, Sharp, who is trained in NMR, probably used NMR as a routine preparative rather than normally analytical tool to determine if she was anywhere near purity. NMR is a highly specialized technique which is neither available nor within the scientific expertise of most scientific investigators. This is especially true for investigators in biomedical research.

Since the Sharp method was beyond the scope of the inventors, they had to develop a method that they could perform on a routine basis. Thus, the present invention was not obvious to chemists who had a serious interest in isolating polyglucosides that are active in the plant system, and the present invention is one that can be carried out in a typical research setting, namely, one with space to set up Bio-Gel columns, a spectrophotometer for readout of the anthrone method for quantitating carbohydrate content, and an HPLC system. Second, the present invention provides a markedly improved method for isolating polysaccharides because of its sensitivity, yields, absence of toxicity, and stabilization of product to a state with increased potency; it is a reasonable method, unlike the prior art.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A heptaglucoside having a molecular weight of approximately 1,000 daltons, capable of interacting with β-glucan receptors on mammalian phagocytic cells.

2. The 2-aminopyridine derivative of the heptaglucoside of claim 1.

3. A therapeutic method for immunomodulation in a subject comprising administering to said subject in need of such immunomodulation the heptaglucoside of claim 1 in an amount sufficient to interact with β-glucan receptors on mammalian phagocytic cells.

4. A method of enhancing an immune response to an antigen in a subject comprising administering to said subject in need of an enhanced immune response an amount of the heptaglucoside of claim 1 in an amount sufficient to enhance the immune response of said subject to said antigen.

5. A method for the treatment of microbial infection, comprising administering to a subject in need of such treatment a pharmaceutical composition comprising a therapeutically effective amount of the heptaglucoside of claim 1, and a pharmaceutically acceptable carrier.

6. The method of claim 5, wherein said microbial infection is a bacterial, fungal, viral, protozoan, helminth or parasitic infection.

7. The method of claim 5, wherein said subject is a human.

8. A pharmaceutical composition useful for inducing the production of antibodies to an antigen in a subject comprising an immunogenically effective amount of an antigen and the heptaglucoside of claim 1 wherein said amount of said heptaglucoside is present in an amount sufficient to enhance the immune response of said subject to said antigen.

9. A process for obtaining from yeast cell walls a biologically active polysaccharide with a molecular weight of approximately 1,000 daltons, which can interact with β-glucan receptors on mammalian phagocytic cells comprising:

(a) solubilizing particulate glucans in said yeast cell walls;

(b) recovering the fraction of step (a) that contains biologic activity;

(c) subjecting the product obtained in step (b) to chromatographic fractionation;

(d) derivatizing the fractionated biologically active product obtained in step (c) with 2-aminopyridine; and (e) subjecting the product obtained in step (d) to chromatographic fractionation.

10. The process of claim 9 wherein step (e) further comprises subjecting said chromatographically fractionated derivatized product from step (d) to high performance liquid chromatography.

11. The heptaglucoside obtained by the process of claim 9.

12. A method for activating the β-glucan receptors on mammalian phagocytic cells comprising derivatizing a biologically active glucan heptaglucoside with 2-aminopyridine and interacting said heptaglucoside with said phagocytic cells.

13. A process for activating the β-glucan receptors on mammalian phagocytic cells comprising:

(a) solubilizing the particulate glucans in yeast cell walls;

(b) recovering the biologically active fraction obtained in step (a);

(c) subjecting the product obtained in step (b) to chromatographic fractionation;

(d) derivatizing the fractionated biologically active glucan product obtained in step (c) with 2-aminopyridine;

(e) subjecting the derivatized product obtained in step (d) to chromatographic fractionation; and (f) contacting the biologically active fraction of step (e) with β-glucan receptors on mammalian phagocytic cells.

14. A method of increasing the potency of a pharmacologically active polysaccharide comprising derivatizing said polysaccharide with 2-aminopyridine.

15. A method for separating biologically active polysaccharide molecules from chemically similar inactive polysaccharide molecules comprising:

(a) solubilizing said polysaccharide molecules;

(b) recovering the active fraction obtained in step (a);

(c) subjecting the product obtained in step (b) to chromatographic fractionation;

(d) derivatizing the fractionated biologically active product of step (c) with 2-aminopyridine; and (e) subjecting the product obtained in step (d) to chromatographic fractionation wherein said polysaccharide is obtained from a cell wall.

16. A method for obtaining the separation of low molecular weight polysaccharide molecules from each other, differing in composition by at least one glucose unit, comprising:

(a) derivatizing said molecules with 2-aminopyridine;

(b) subjecting the products obtained in step (a) to chromatographic fractionation; and (c) recovering the desired fraction obtained from step (b).

17. A process for obtaining the separation of isomers of low molecular weight polysaccharide molecules comprising:

(a) derivatizing said molecules with 2-aminopyridine;

(b) subjecting the products obtained in step (a) to chromatographic fractionation; and (c) recovering the desired fraction from step (b).

* * * * *